(12) United States Patent
White et al.

(10) Patent No.: US 11,581,081 B2
(45) Date of Patent: *Feb. 14, 2023

(54) SESSIONS AND GROUPS

(71) Applicant: NIKE, Inc., Beaverton, OR (US)

(72) Inventors: Kristen L. White, Portland, OR (US);
Michael L. Orenstein, Portland, OR (US); Jenny Campbell, Beaverton, OR (US); Christina S. Self, Portland, OR (US); Elizabeth Walker, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/031,482

(22) Filed: Sep. 24, 2020

(65) Prior Publication Data
US 2021/0012099 A1 Jan. 14, 2021

Related U.S. Application Data

(63) Continuation of application No. 15/608,529, filed on May 30, 2017, now Pat. No. 10,803,305, which is a
(Continued)

(51) Int. Cl.
G16H 20/30 (2018.01)
G06F 16/487 (2019.01)
(Continued)

(52) U.S. Cl.
CPC ........... *G16H 20/30* (2018.01); *A61B 5/0022* (2013.01); *A61B 5/1118* (2013.01);
(Continued)

(58) Field of Classification Search
CPC ................................................ G06K 9/00348
(Continued)

(56) References Cited

U.S. PATENT DOCUMENTS

2011/0054359 A1  3/2011  Sazonov et al.
2012/0150074 A1  6/2012  Yanev et al.
(Continued)

FOREIGN PATENT DOCUMENTS

CN   103154954 A    6/2013
JP   2005115799 A   4/2005
(Continued)

OTHER PUBLICATIONS

Aug. 22, 2014—(WO) ISR and WO—App No. PCT/US2014/052360.

*Primary Examiner* — Thomas J Hong
(74) *Attorney, Agent, or Firm* — Banner & Witcoff, Ltd.

(57) ABSTRACT

Athletic activity may be tracked while providing encouragement to perform athletic activity. For example, energy expenditure values and energy expenditure intensity values may be calculated and associated with a duration and type of activity performed by an individual. These values and other movement data may be displayed on an interface in a manner to motivate the individual and maintain the individual's interest. The interface may track one or more discrete "sessions". The sessions may be associated with energy expenditure values during a duration that is within a second duration, such as a day, that is also tracked with respect to variables, such as energy expenditure. Other individuals (e.g., friends) may also be displayed on an interface through which a user's progress is tracked. This may allow the user to also view the other individuals' progress toward completing an activity goal and/or challenge.

20 Claims, 16 Drawing Sheets

Related U.S. Application Data continuation of application No. 14/466,655, filed on Aug. 22, 2014, now Pat. No. 10,216,985.

(60) Provisional application No. 61/869,610, filed on Aug. 23, 2013.

(51) Int. Cl.

| | |
|---|---|
| *A61B 5/00* | (2006.01) |
| *G06V 40/20* | (2022.01) |
| *A61B 5/11* | (2006.01) |
| *G04F 10/00* | (2006.01) |
| *G06Q 50/00* | (2012.01) |
| *G06F 16/48* | (2019.01) |
| *G16H 40/67* | (2018.01) |
| *G16H 40/63* | (2018.01) |

(52) U.S. Cl.
CPC .......... *A61B 5/4866* (2013.01); *A61B 5/7435* (2013.01); *G04F 10/00* (2013.01); *G06F 16/487* (2019.01); *G06Q 50/01* (2013.01); *G06V 40/25* (2022.01); *A61B 5/681* (2013.01); *A61B 5/6802* (2013.01); *A61B 5/6807* (2013.01); *G06F 16/489* (2019.01); *G16H 40/63* (2018.01); *G16H 40/67* (2018.01); *Y02A 90/10* (2018.01)

(58) Field of Classification Search
USPC ........................................................ 434/246
See application file for complete search history.

(56) References Cited

U.S. PATENT DOCUMENTS

| | | |
|---|---|---|
| 2012/0283855 A1 | 11/2012 | Hoffman et al. |
| 2013/0106603 A1 | 5/2013 | Weast et al. |
| 2013/0184613 A1 | 7/2013 | Homsi et al. |
| 2013/0191034 A1 | 7/2013 | Weast et al. |

FOREIGN PATENT DOCUMENTS

| | | |
|---|---|---|
| JP | 2009213654 A | 9/2009 |
| JP | 2012137930 A | 7/2012 |
| JP | 2012525220 A | 10/2012 |
| JP | 2013503694 A | 2/2013 |
| JP | 2013513439 A | 4/2013 |
| JP | 2016538088 A | 12/2016 |
| WO | 2012021507 A2 | 2/2012 |
| WO | 2012082782 A1 | 6/2012 |
| WO | 2013109780 A2 | 7/2013 |

SESSIONS AND GROUPS

CROSS REFERENCE TO RELATED APPLICATIONS

This application is a continuation of U.S. patent application Ser. No. 15/608,529, filed May 30, 2017, which is a continuation of U.S. patent application Ser. No. 14/466,655, filed Aug. 22, 2014, now U.S. Pat. No. 10,216,985, which claims the benefit of, and priority to, U.S. Provisional Patent Application No. 61/869,610, filed Aug. 23, 2013. The content of each of these applications is expressly incorporated herein by reference in its entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to calculating energy expenditure values. In certain embodiments, energy expenditure points may be calculated. One or more devices may use an accelerometer and/or other sensors to monitor activity of a user. Under certain implementations, a user may earn energy expenditure points for different activities.

In some embodiments, the present invention can be partially or wholly implemented on a computer-readable medium, for example, by storing computer-executable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

FIG. 7A shows a UI having a listing of a plurality of sessions, in which a first portion of sessions are grouped according to at least one variable and a second portion of sessions are not grouped in accordance with at least the same variables; FIG. 7B shows an example view of a UI displaying athletic data of at least one session; FIG. 7C shows an example view of a UI displaying athletic data relating to a collection of sessions grouped together, such as by a common activity, location or other variable; and FIG. 7D shows an example UI displaying a plurality of discrete sessions that are grouped together;

FIG. 8A shows an example view of an IU that allows a user to set variables; FIG. 8B is an example view of an UI configured to permit a user to select an activity; and FIG. 8C is an example view that provides an example representation of an activity being designated by a user;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
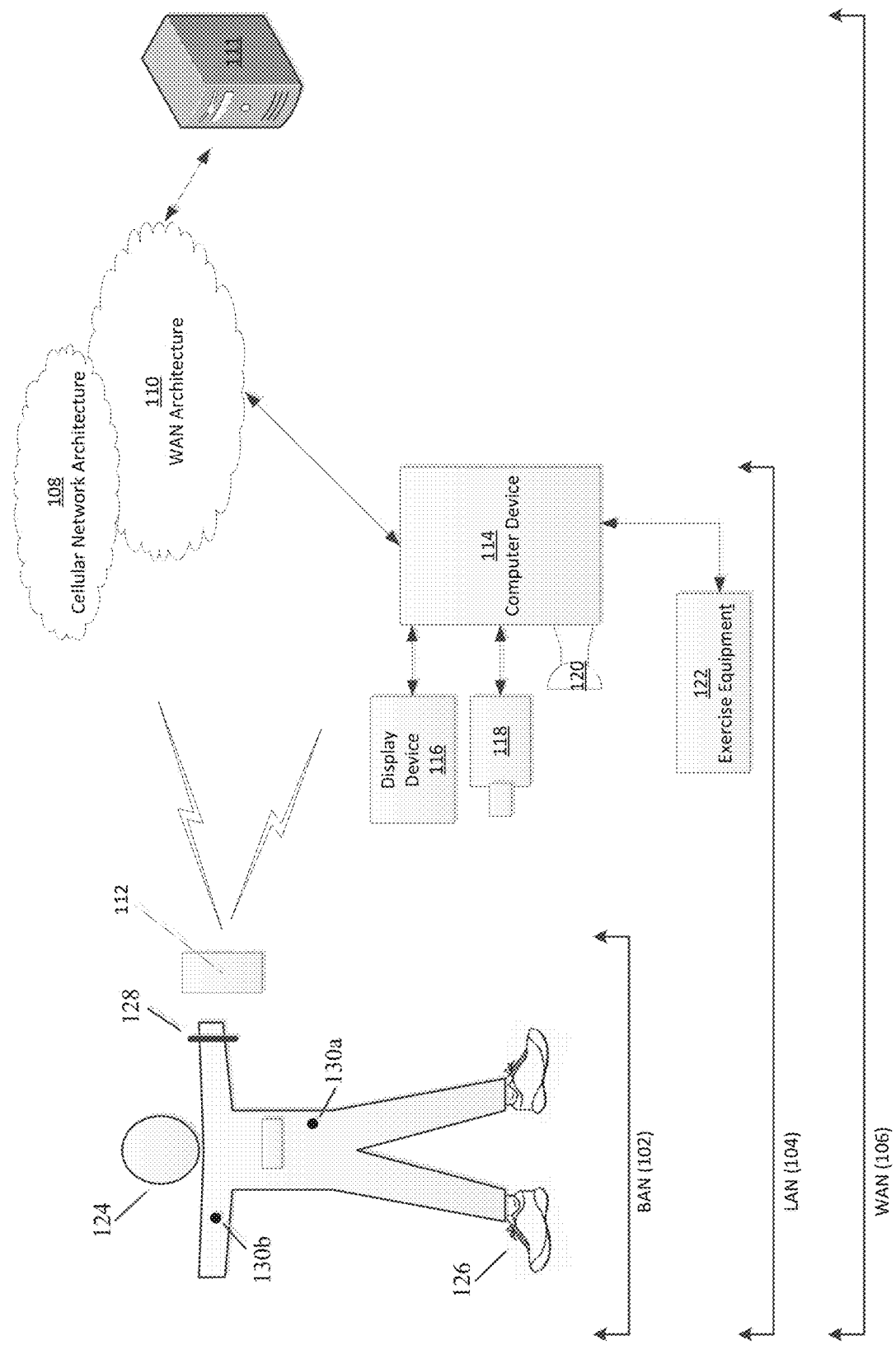
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
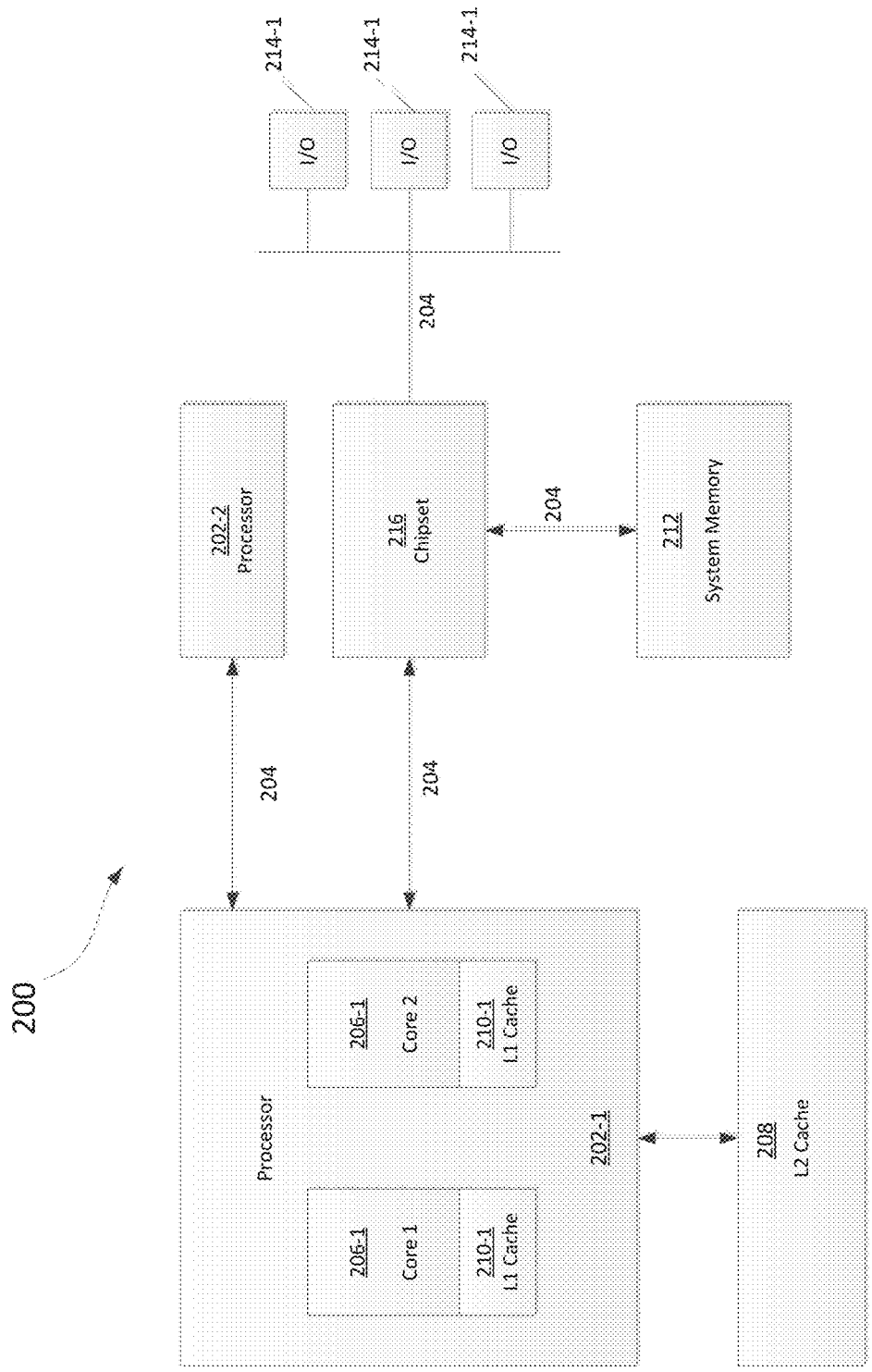
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
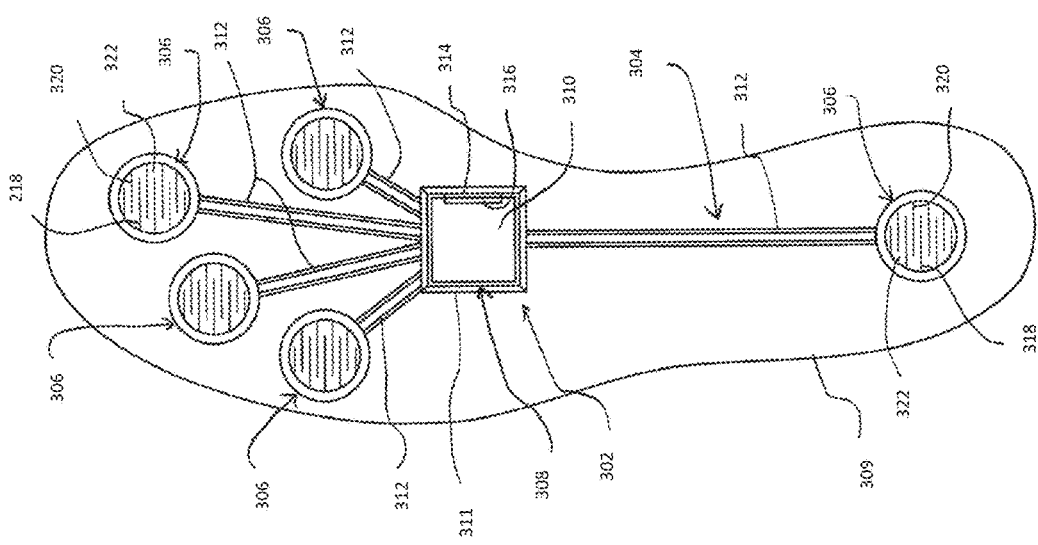
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
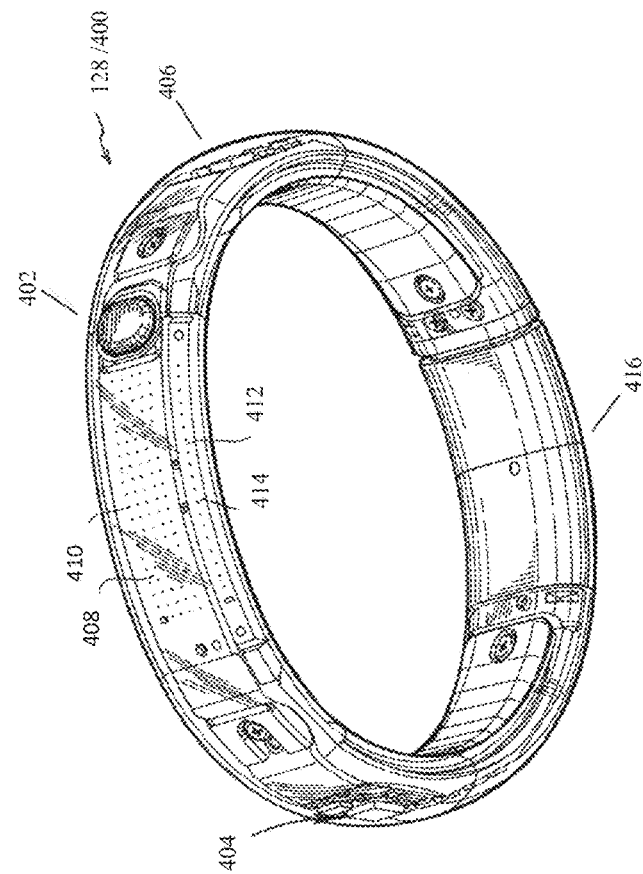
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
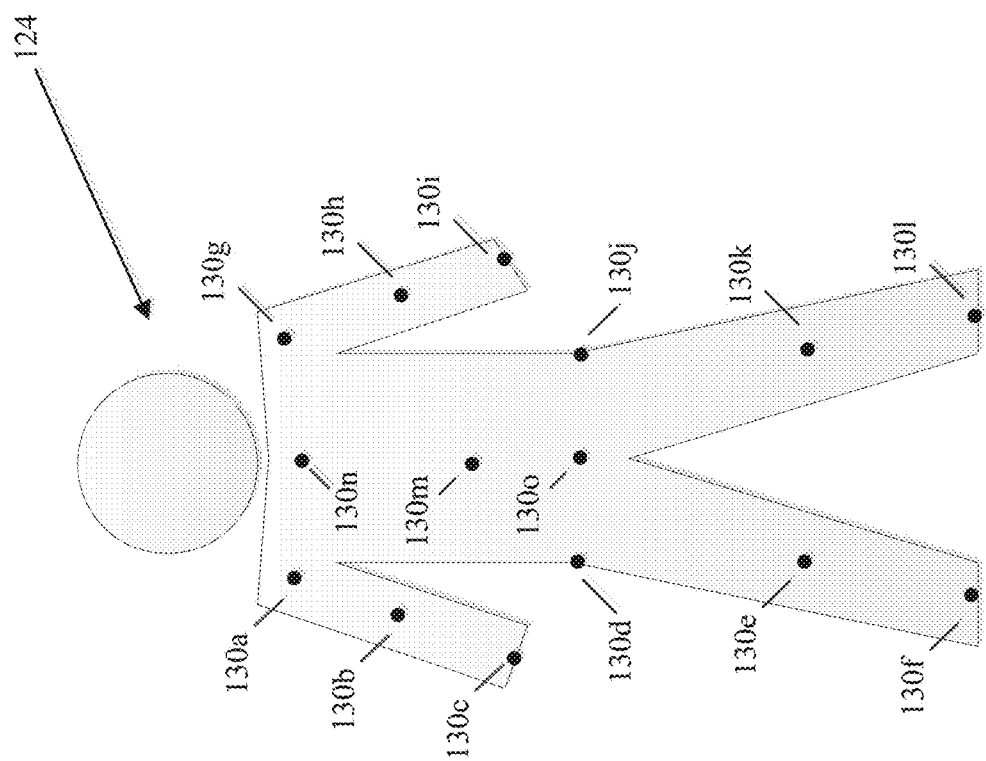
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

II. Energy Expenditure Point Calculations

Figure 6:
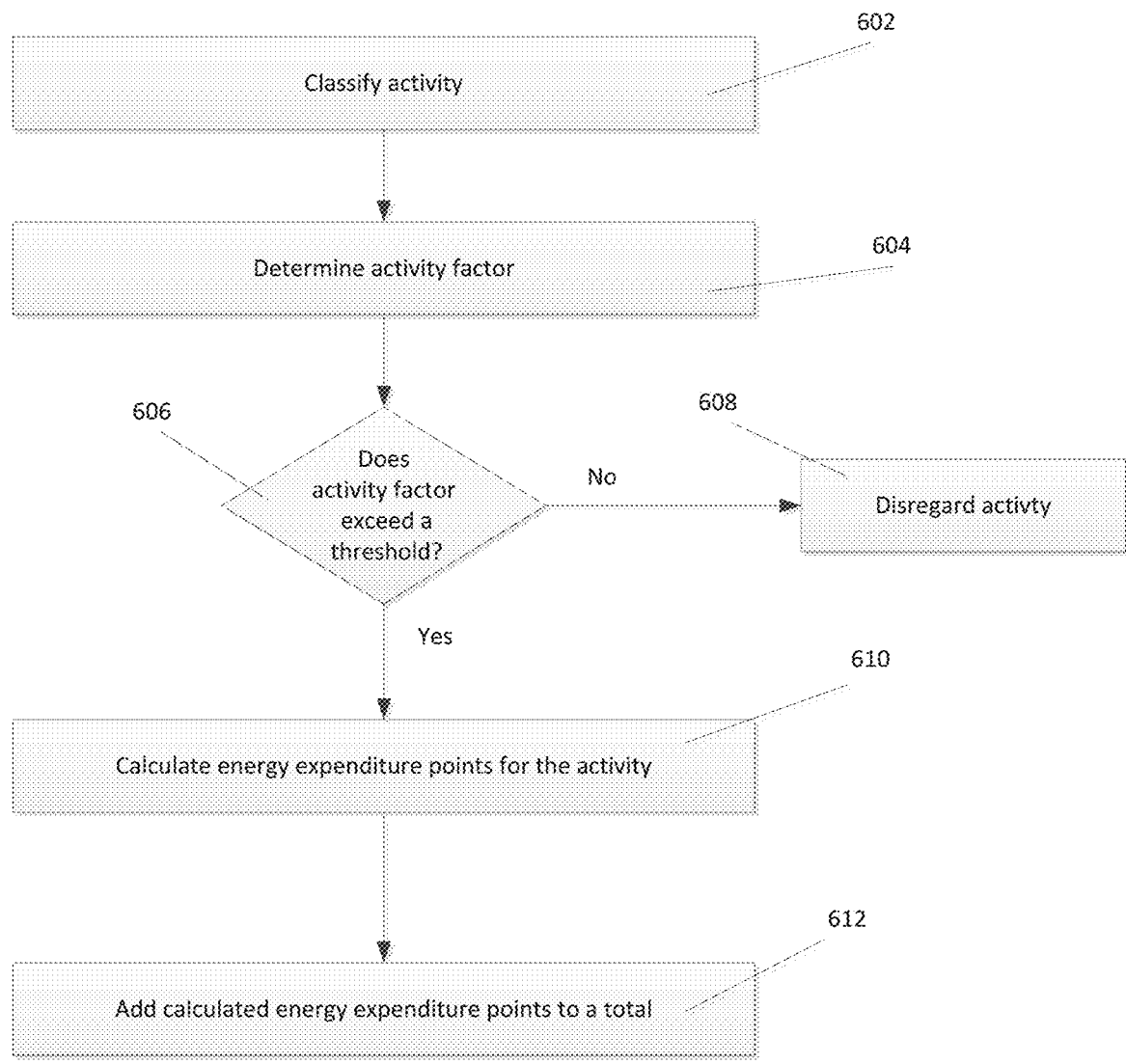
FIG. 6 illustrates a method for calculating energy expenditure values, such as points, in accordance with an embodiment of the invention.

FIG. 6 illustrates a method for calculating energy expenditure values, such as points, in accordance with an embodiment of the invention. Certain embodiments may classify physical motions of a user. For example, at illustrative step 602, one or more activities may be classified. A system may process data received from one or more of the sensors described above to attempt to classify a user's activity. For example, a system may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 128) may be utilized in the formation or refinement of a first activity template; however, a second group of sensors (e.g., sensors 138 and a sensor included in portable electronic device 112) may be utilized in the formation or refinement of a second activity template. In yet further embodiments, a third group of sensors, may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 602 may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified. Some embodiments may utilize only templates for running and walking and a best first approach is used to determine whether the user is running or walking.

After at least one of user's 124 activity is classified, step 604 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 602, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

Energy expenditure point calculations may be used in connection with games and competitions. Some games and competitions may limit awarding energy expenditure points for activities that have relatively low activity factors. In some embodiments, awarding energy expenditure points for activities that have relatively low activity factors may also be limited all of the time or in other situations. In step 606 it may be determined whether the activity factor exceeds a threshold value. For example, an exemplary threshold value may be 1.0, 2.0 or 3.0. In another embodiment, the threshold value may equal 2.8. Different games and competitions may use other threshold values. When the activity factor does not exceed the threshold, step 608 may be implemented to disregard the corresponding activity and not use the activity when calculating energy expenditure points.

Another embodiment could have the threshold generally applied, but not when games or competitions are underway, or at least certain games or competitions. The games or competitions may be based on all points. In another embodiment, a threshold may always apply even to games and competitions. In another embodiment, different thresholds may apply by activity, game and/or competition, e.g., one for running briskly, one for running, one for walking, and a default.

In various embodiments of the invention, activity factors are used to calculate energy expenditure points. After at least one of user's 124 activity is classified, in step 610 energy expenditure points may be calculated. The use of energy expenditure points allows for comparison of activity levels and may promote collaboration among users, normalize for competition among users of different capabilities, and otherwise encourage activity. In one embodiment, energy expenditure points are calculated as follows:

$$EEPs = AF * duration \qquad \text{(equation 1)}$$

Wherein:
EEPs=energy expenditure points
AF=activity factor determined in step 604
duration=duration of the activity classified in step 602

Step 610 may be performed at a device that includes sensors that monitor activity and/or at another device that includes a processor, such as portable electronic device 112 or server (see, e.g., 111). In alternative embodiments equation 1 may be modified to include other factors, a scalar and/or a different combination of terms.

In some embodiments equation 1 may be modified to include a scalar that is multiplied by the activity factor and duration. The scalar may be selected so that typical energy expenditure points fall within a desired range. The range of points may be desired for various games or competitions. The scalar may also represent an intensity of the activity. For example, a first scalar may correspond to brisk running and a second scalar may correspond to running at a moderate pace. In alternative embodiments additional activity templates and activity factors may be used and may correspond to the various intensities of running or walking.

Variations of equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total for their overall energy expenditure. Some point totals may be maintained separate from an overall point total.

Alternative embodiments of the invention may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity points or energy expenditure points and steps. Calculating values that are functions of activity points or energy expenditure points and other variables may be used to compare the efficiencies of various activities. For example, an equation may be used to determine that taking steps at a faster pace may result in activity points or energy expenditure points accumulating at a faster per step pace. Another exemplary equation may determine activity points or energy expenditure points per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity points or energy expenditure points is displayed to a user via display 408 or a display that is part of a mobile device.

After the energy expenditure points are calculated, the calculated points may be combined, such as being added, to a total in step 612. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points awarded since the beginning of use of a device or start of a program. The total for any given time period may represent points earned for several activities. For example, in a day a user may receive points for walking, jogging and sprinting during different time periods. As mentioned above, the points earned for each activity may be a function of a corresponding activity factor.

As indicated above, systems and methods may be variously implemented to determine a rate that a user accumulates activity points or energy expenditure points. In one embodiment, energy expenditure intensity values may be calculated for one or more time periods. The plurality of time periods may be within a unitary time frame, such as a minute, 5 minutes, 10 minutes, an hour, or a day. Those skilled in the art will appreciate that these are merely examples. In certain embodiments, a user may designate or alter the duration and/or quantity of time periods and/or time frame.

Certain embodiments may organize data collected at different time periods into a collection. As one example, data collected during time periods within a time frame may be designated as a "session". As used herein, a session refers to a discrete collection of activity data collected from a user during a designated time period and/or activity. Activity data, however, may be automatically collected and/or organized into a "session". Further, activity data is not required to be designated as being a session or type of session during its collection. For example, a UI may be configured to permit a user to designate past activity data as being associated with a specific activity, sport, event or motion.

FIGS. 7A-D show example session user interfaces (which may be referred to herein as a session UI or UI). Looking first to FIG. 7A, session UI 700 may be configured to display activity data collected in a plurality of sessions. For example, in one embodiment, the user interface 700 may indicate that past activities (which may be stored as raw and/or processed data, including for example, energy expenditure points or values) were collected.

Figure 7D:
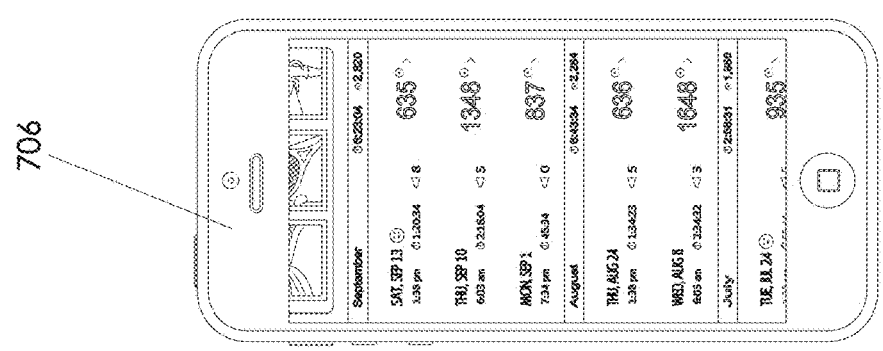
FIGS. 7A-7D show example views of a UI that may be configured to provide athletic data associated with a session and further configured to be interacted with by a user in relation to session information; Specifically.
Figure 7C:
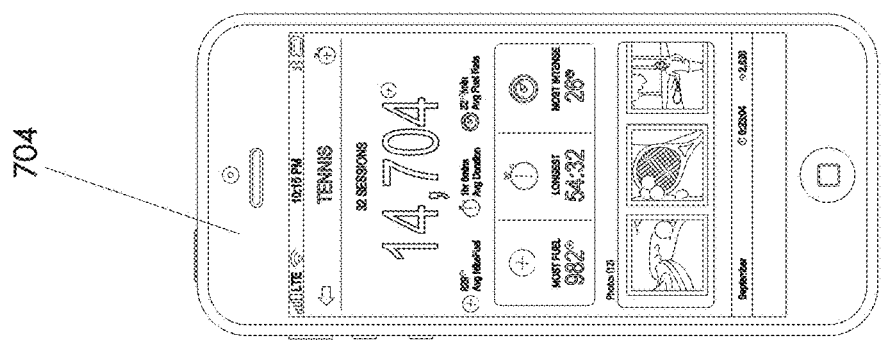
Figure 7B:
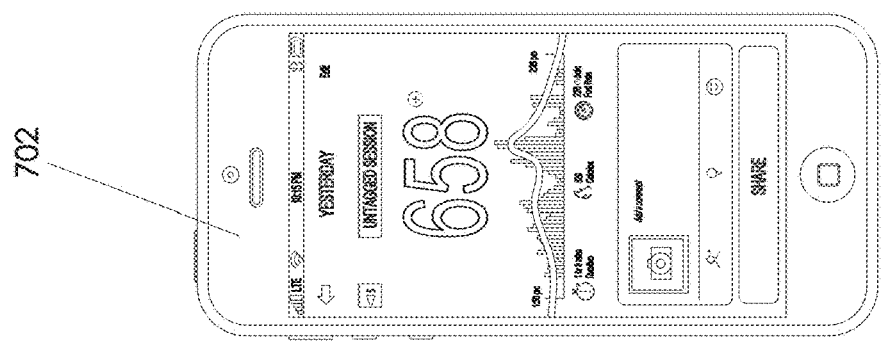
Figure 7A:
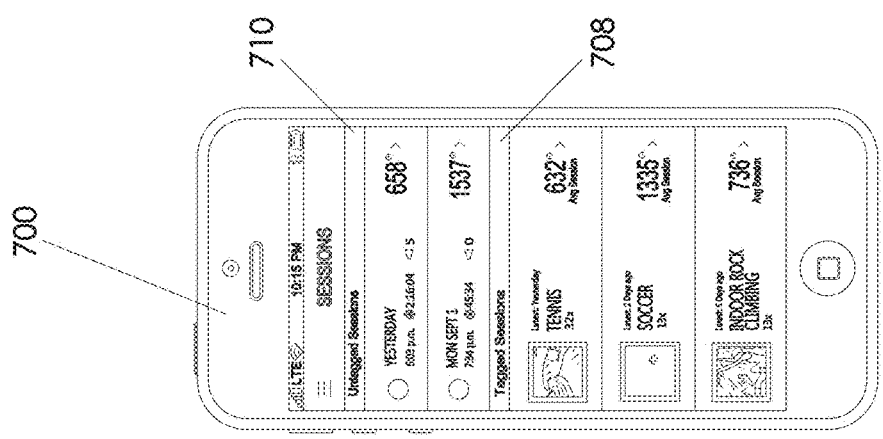

As illustrated in FIG. 7A, the activities may be organized into sessions. Example sessions may be organized by an activity type, which may be provided or otherwise organized by a genus and/or species of a larger categorization. As shown in FIG. 7A, example sessions may be grouped as, for example, a TENNIS session or a SOCCER session. One or more of the activities may have an activity type designation associated with them. These sessions may be referred to as "tagged" sessions and may be listed in a separate listing area 708 for tagged sessions. Some sessions may have been automatically labeled, for example, based on one or more data items, such as a signal template, proposed or actual location of the activity, a calendar event or other data containing scheduling of the activity, time/date of the activity, and/or the list of friends associated with the activity, if any (including sensor data indicating the presence of one or more other individuals.

Other sessions may not have specific variable, such as an activity type designation, associated with them. These sessions, at least in relation to the specific variable, may be referred to as "untagged" sessions and may be listed in a separate listing area 710 for untagged sessions. For example, as can be seen in FIG. 7A, the session labeled "YESTERDAY" does not have an activity type designation associated with it, however, may be organized by another variable, such as using a representation of the date. In one embodiment, a user may be provided with UI having a mode where a stop and start are configured to be enabled based on a user input and/or automatically triggered based upon one or more inputs, such that an activity can be captured as a session and labeled with the time and or date of the activity. In another embodiment, a session may be started automatically, based on sensor data or location information. The sensor or location information may come from device 400 or from a second device, such as a mobile phone. Sensor data, which may be used to collect athletic data and/or determine the occurrence or characteristic of a session, and/or determine possible variables associated with a session may come from multiple devices.

In one embodiment, a user may tag or otherwise a previous sessions to assign them an activity type designation. For example, a user may select a session, via the user interface 700, in order to view details of the session, as shown in FIG. 7B. In the example illustrated in FIG. 7B, the user has selected the "YESTERDAY" session and details of that session are displayed in interface 702. Interface 702 may display details such as the duration of the session, athletic data, e.g., energy expenditure points accumulated in the session, the number of calories burned. The number of activity points or energy expenditure points earned during the session may also be displayed. Other types of information not depicted in FIG. 7B may also be displayed, such as location the session took place, the start and stop time of the activity, etc. In an embodiment, a user may be able to tag a session to assign an activity type designation. For example, as shown in FIG. 7C, a user has selected to tag an unlabeled session as TENNIS. Tagging a session may be accomplished through several methods, including selecting the tag from a list of activity types presented via a user interface or typing the name of an activity type and searching, for example. Further embodiments may allow any designation which may or may not be one available listing for selection. In certain embodiments, no listing may be provided. Assigning an activity type designation to a session may be advantageous to a user in certain embodiments. For example, once a session is designated as a known activity type, various calculations may be selected, augmented, and/or improved, such as based upon the nature of the activity.

In addition, various statistics can be further improved or provide benefit to a user. For example, by tagging the session as "TENNIS", the session can be more readily compared to other sessions of the same activity type, either from the user and/or other individuals and/or groups. Some or all sessions of a particular activity may be manually or automatically grouped together for display or for analysis. FIG. 7C illustrates example statistics that may be collected and displayed. Those skilled in the art would recognize that these are just examples of the many types of statistics that may be of interest to a user and could be displayed in interface 704. A user may want to see how the tagged session compares to others, for example, or the length of the session or the number of calories burned. In addition, by tagging the session, a count and other statistics related to the type of activity can be made available. In FIG. 7C, in the interface 704, it can be seen that the user has 32 sessions designated as "TENNIS".

A user and/or other individuals or groups (e.g., coaches, trainers, friends, teammates, etc.) may also be able to add additional information to the session. For example, it may be advantageous with some types of activities to collect additional statistics. A user who does rock climbing may collect change in altitude while a swimmer may not. A user may provide additional information or the additional information may be collected from sensors on the device or other devices. For example, a calorie count is depicted in FIG. 7C, but other data such as steps taken, average heart rate or maximum heart rate may be displayed in some embodiments.

In FIG. 7D depicts a user interface 706 in which a user can view, such as via a scrolling user input received down during display of information about a particular activity type. As depicted in 706, a history of sessions for the activity type may be displayed, along with statistics related to each of the sessions. The sessions may be organized based on time/date of the session or the sessions may be organized in other ways advantageous to the user, such as by duration of session or by energy expenditure points or other metrics.

As another example, an input may designate that future activities, such as a scheduled soccer game or running event, is a "session" or collection of related data. One or more designations may be suggested or even automatically generated from electronic data, such as information stored in relation to a calendar application on an electronic device. The electronic data may be stored on the same device comprising a sensor from which at least a portion of the motion data is collected from and/or configured to receive data from at least one of the sensors. One or more designations may be suggested or automatically generated through use of a signal template.

Figure 8C:
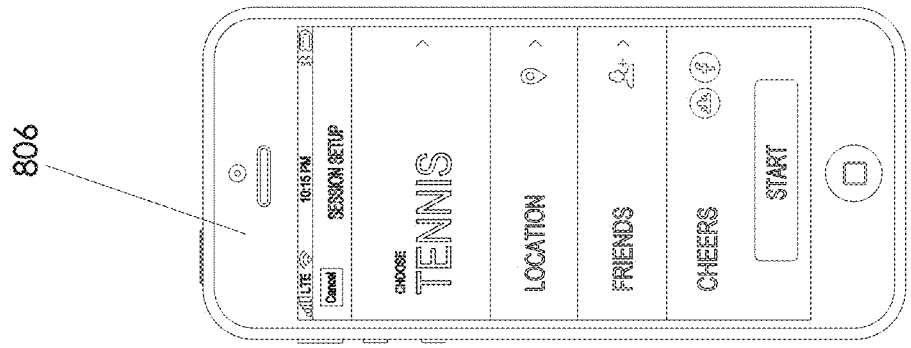
FIGS. 8A-C show example views of a UI that may be configured for interaction by a user in relation to setting up a session, which may be utilized, prior to, during, or after the athletic data for the session is collected and/or the session occurs; Specifically.
Figure 8B:
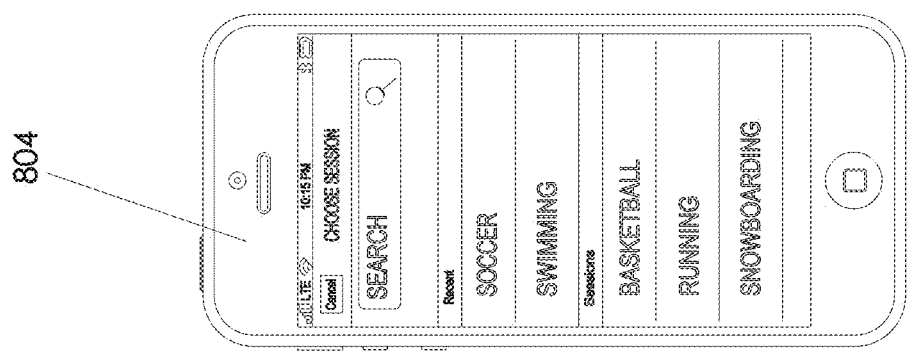
Figure 8A:
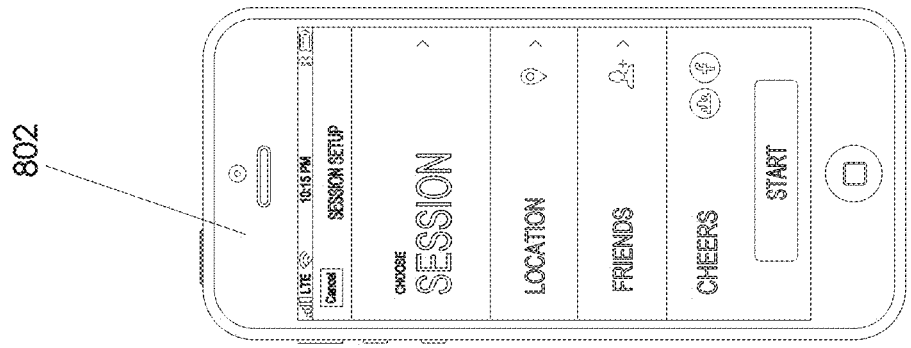

FIG. 8A-C illustrates example views of a UI that may be configured for interaction by a user in relation to setting up a session, which may be utilized, prior to, during, or after the athletic data for the session is collected and/or the session occurs. As one example, the example UI may be used as part of a user selecting to start a session and choosing a variable, such as an activity type. FIG. 8A illustrates an example in which a user may be prompted at prompt 802 to choose a session activity type (which may be another variable in different embodiments). FIG. 8B illustrates an example user interface that may be presented after the user chooses to start a session and/or desires to tag or otherwise associate a variable, such as an activity type, to a past or current session. In FIG. 8B, several session activity type designations 804 may be presented for selection by the user. The session designations may comprise recent activities that the user has completed. The session designations may also list activity types that the user has not participated in before. For example, "SNOWBOARDING" may be listed, even though the user may not have chosen such an activity before. The items listed in the sessions list of FIG. 8B may be session types input by other users of the application and may be filtered based on any number of parameters, such as location, date, and various parameters related to the user, such as age and/or other demographic information, for example, which may be obtained or derived from one or more different sources.

In some embodiments, the sessions filtering may exclude types of sessions that would be unlikely for the user to select, based on parameters related to the user or the environment, such as snow skiing when the user is located in a warm climate.

A different session list may be presented to first time users or users who have used the application a limited number of times. This may help a new user become familiar with the types of session designations available or it may be used in the absence of certain information about the user, his/her activity history or other parameters, such as location, user age, etc. In some embodiments, a user may input their own session designations. For example, a user may want to track a session for an activity not listed in the session list. A user may enter, via the user interface, the name to be used as the session designation and store it for future use. The input session designation may be shared or made available to other users. Further, data from different sessions, either from the user and/or other individuals and/or groups may be used to suggest or provide for selection certain activities or other variables for selection. In some embodiments, the session designation may be automatically selected or suggested, based on sensor data, such as location, friends nearby, time or date, for example. Sessions may also be initiated, augmented, paused, and/or terminated by a plurality of different inputs, including a user input, such as by a user using an interface on a sensor device, such as button 402 on device 400. Those skilled in the art will realize that soft buttons or user input devices, including on a touch-enabled device may be utilized. In further embodiments, sensor data, such as data indicating the user has remained stationary or below a threshold, may be used to terminate, pause or otherwise augment a session. In this regard, a session may be initiated on a first device, such an appendage-worn device, however, may be augmented, terminated, or otherwise altered based upon a user input and/or data received from another device, such as a mobile phone. For example, the user may provide a manual user input providing a variable, e.g., athletic activity type, and/or usage data may indicate that the user is on a telephone call or otherwise using a device and this data may be used at least in part to pause or end or otherwise augment the session.

Referring now to FIG. 8C, the user interface shows an example in which the user has selected "TENNIS" (or tennis has otherwise been selected), as is shown at 806. As can be seen in FIG. 8C, the user may be presented with the option to start the session after selecting the session. It should be understood that the user may choose to start the session later. Additionally, the user may use an interface such as those depicted in FIG. 8A-C to assign a session to an activity type after at least a portion of the activity has taken place or while the activity is in progress. For example, a user may forget to start a session before starting an activity and can then choose the session after the activity has started or after the activity has concluded.

In another embodiment, motion data collected within a geographic area may be used to associate that data with a specific sport or activity. For example, GPS data (which may be obtained from the same or different device that obtains at least a portion of the motion data) may be utilized to determine that the user is or was within a geographic area. Thus, data collected within that area may be associated together as a session or other collection. In yet another embodiment, a combination of information may be used to designate a collection of motion data, such as a session. In one embodiment, motion data obtained at or within a proximity to a geographic location or area during one or more time frames (e.g., data collected within 500 feet of a soccer field during the hours of 2-4 pm on a Saturday) may be associated together, such as classified as a soccer session. Geographic data may be obtained from GPS, triangulation of communication signals, presence of other signals, such as detection of a certain sensor, and/or by manual indication via a user input. Geographic data may be suggested to a user, for example, based on best available sensor data. Additionally, a user may select from a list of suggested locations. In certain embodiments, such data may only be grouped as a soccer session if the quantity of steps, calories burned, calories burned per unit of time, or other variable reaches a threshold. The threshold may be a binary determination such that none of the data will be deemed to be associated with the activity type if it's not met, yet others may determine only that time frame meeting a threshold may be deemed the activity type. Those skilled in the art will realize that a multitude of different combinations may be used.

Figure 9:
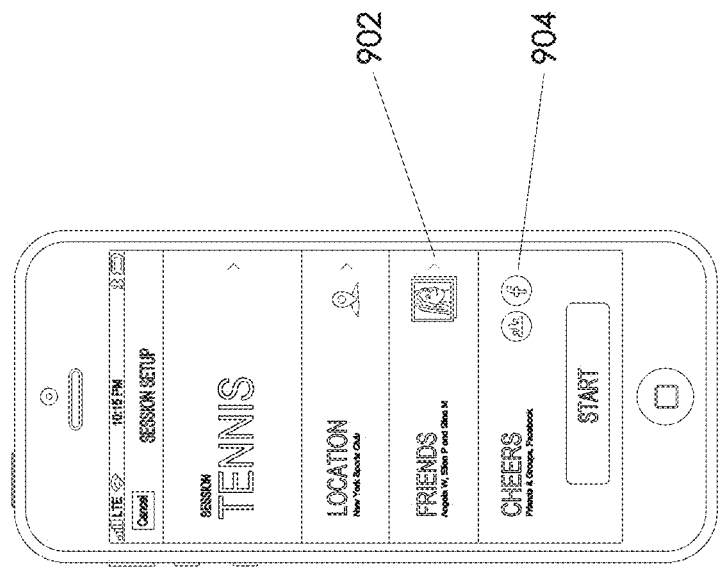
FIG. 9 shows an example view of a UI that may be configured to allow a user to input variables relating to one or more sessions.

Referring now to FIG. 9, in some embodiments, a user may tag, input or select friends 902 from a list and add them to the session as session information. This may be useful to a user when referring back to the session, so that they can recall who participated in the session with them, provide comparisons, forming, reforming, or dividing individuals into groups, such as teams or leagues Motivation—Celebrations & Cheers In addition to selecting or inputting friends who participated in a session as session info, a social aspect, such as via a network may be selectable or otherwise invoked so that other individuals and/or groups, such as friends, coaches, teammates, or league members in those networks can be informed about the session, for example, and provided with statistics or milestones during or after the session. When a user completes a goal, reaches a milestone, completes an objective, makes progress or completes an improvement run, for example, a user may be provided with encouraging or celebratory messages. Alternatively or additionally, cheers, words of encouragement and/or other messages may be provided pre- or mid-run. These messages may include audio, video, images, animated images, tactile or haptic feedback (e.g., vibrations) and the like. In one or more arrangements, the celebratory messages may include audio and/or video messages from a celebrity such as a well-known athlete. In other embodiments, the messages may be received from friends in one or more of the social networks in the session setup. The user may be allowed to configure when such messages are to be rendered and conveyed to the user. For example, the user might not want celebratory messages during activities and thus, may indicate a preference that all messages be played after a workout or during non-workout times. Accordingly, the user may specify when messages are not to be conveyed as well. Additionally or alternatively, celebratory messages may include sound effects such as a crowd cheering, a bullhorn, cowbell ringing, vuvuzela blasts, fireworks exploding and slot machine jackpot sounds, among others. FIG. 9 illustrates an example user interface providing for a CHEERS setting 904 in a session setup interface. A workout session announcement may be posted or otherwise provided to an on-line community such as a user's social networking site or conveyed through an on-line community such as a social networking service (e.g., TWITTER, Facebook) before, during or after a workout. The posting may be provided based on sensor data, e.g., location, time, and/or other data. The announcement may indicate a type of workout that the user is pursuing (e.g., a marathon training run) and a message encouraging other users (e.g., friends and family) to leave comments or indicate approval (or disapproval) of the workout. A number of comments or indications of approval may be displayed in conjunction with the announcement as well. In some arrangements, multiple types of feedback and/or feedback from multiple different and/or distinction on-line communities or remote network sites (e.g., social networking services) may be aggregated to determine the amount of feedback received. For example, a number of comments may be added to a number of approval indicators received. In other arrangements, each type of feedback may be counted separately. Additionally or alternatively, only positive feedback or feedback matching one or more predefined rules or parameters (e.g., type of content, words, characters, symbols, etc. used in the feedback, identity of an author/ commenter and the like) may be counted towards the amount of feedback. In still other examples, the type of content or message selected for delivery to the user may be based on matching one or more predefined parameters or rules other than or in addition to an amount of feedback. For example, such parameters or rules may include type of content (video, audio, text), words, characters, symbols, etc. used in the feedback, identity of an author/commenter and the like.

Determining an amount of feedback received may include receiving the comments from an on-line community (e.g., social networking site) and counting the amount of feedback received (e.g., a number of comments). In another example, determining the amount of feedback may include receiving an indication of a number of comments or feedback received in response to the posted workout information. In other examples, determining the amount of feedback may be performed by another device. The other device may then provide the determination of the amount of feedback to an athletic monitoring system. The other device may also be configured to select the content (e.g., sound effect, video, text, haptic feedback) to be provided to the user. Providing the determination of the amount of feedback may also be performed from one software or hardware module of a device (e.g., an athletic performance monitoring device) to another software or hardware module of that same device. Provision of the determination of the amount of feedback may also include storage of the determination of the amount of feedback in memory.

According to some arrangements, the determination of the amount of feedback and the selection of the content may be performed by different devices such as an athletic performance monitoring service and an athletic performance monitoring device. Alternatively, the determination and the content selection may be performed by the same device. In still other arrangements, the determination of the amount of feedback and/or the selection of content may be performed by the on-line community (e.g., the social networking system).

In some embodiments, motion data, such as the data described above or anywhere throughout this disclosure, may only be classified as a session if at least a portion of the data meets a criterion. For example, if energy expenditure intensity values for at least a portion of the activity does not meet a threshold, then a portion or all of the data may not be classified within a session. Users may be able to tag the sessions as being within certain activity, either during or after collection of the data.

Energy expenditure values, including energy expenditure intensity values, may be displayed, such as on a portable electronic device, as a function of time. In one implementation, data of a session may be displayed. A first value collected during a first time period may be displayed as a first variation of a display characteristic based upon exceeding a first threshold and a second value (which may be collected during a second time period within the same session) may be displayed as a second variation of the display characteristic based upon exceeding the second threshold. The display characteristic may relate to at least one of: color, size, or shape, for example.

Further embodiments may organize similar collections of data, such as session data, together. For example, "soccer sessions" may be organized such that a user may readily view trends from different sessions, which may be collected from motion data of different times and/or locations. Further, a first session may have been collected by one or more sensors that were not utilized to obtain motion data during another session. One or more sessions may be designated by markers on a map.

Figure 10:
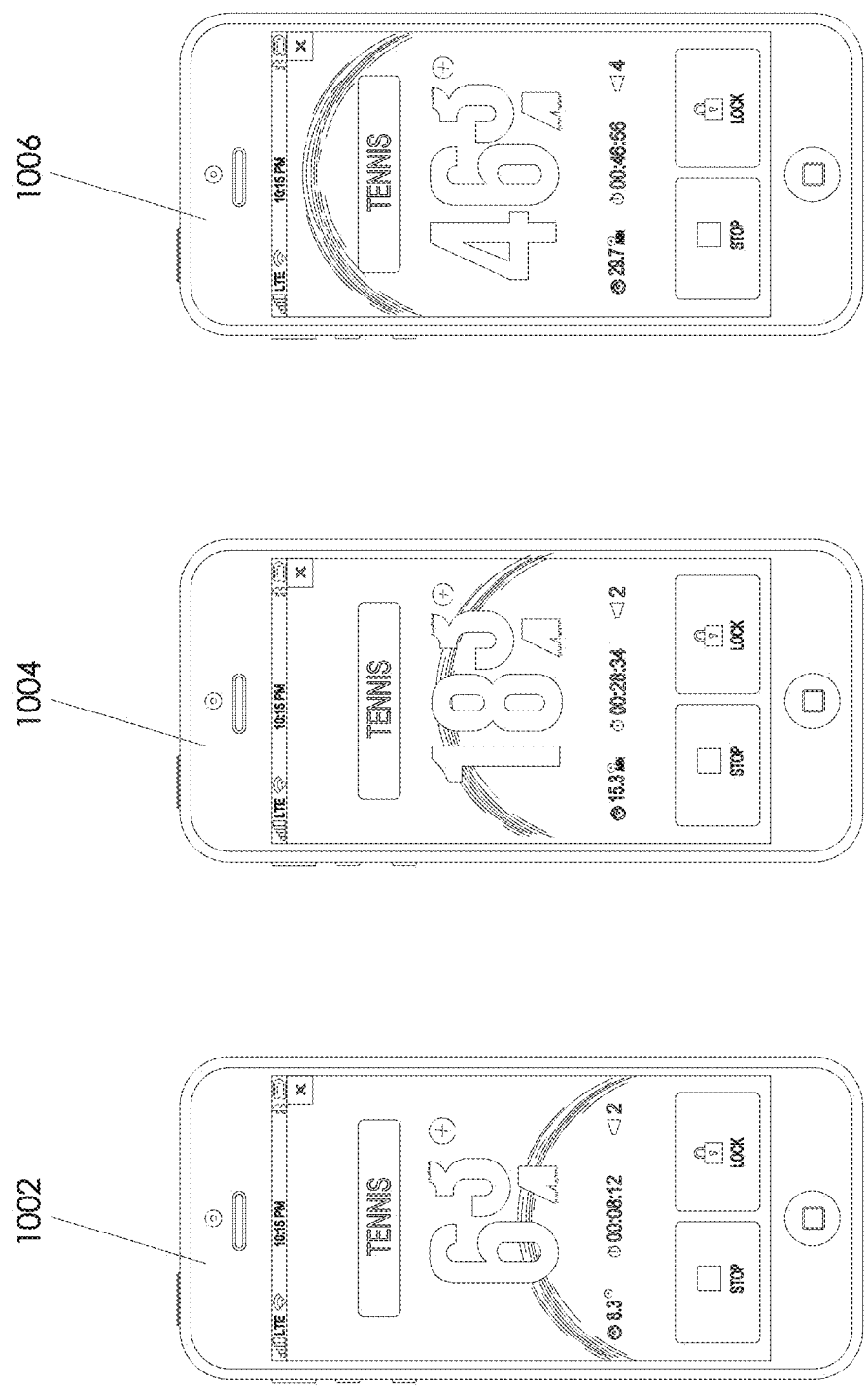
FIG. 10 shows an example view of a UI that may be configured to alter the visual representation or visual indicia of a display based on data collected during one or more sessions.

In one embodiment, one or more calculations of the motion data may occur in real-time, or as the data is being collected. In one embodiment, energy expenditure values may be displayed on an output of an electronic device. FIG. 10 illustrates a user in a TENNIS session and depicts energy expenditure value increasing as the session progresses. In one embodiment, an accumulation of energy expenditure values may be displayed and other information, such as color variations may indicate an intensity level, such as based upon the quantity of energy expenditure of the user as a function of time and/or a total quantity for a designated session or time. For example, a user may wish to achieve a certain goal for the entire session and yet a minimum goal or standard throughout a unit of time for at least a portion of the session, such as 1500 calories burned for the session but at least a minimum of 20 calories per minute for at least 90% of the session duration. Looking to example user interface 1002 of FIG. 10, the energy expenditure indicated is 63 to 64 points. This may be considered a low energy expenditure in one embodiment and, as such based on one embodiment, may be presented in association with a first visual indicia, e.g., a red background. Other effects may be applied, such as a partial background coloring to indicate a percentage of progress toward a goal or a standard. As can be seen in 1002, a colored background, for example a red background area, may be depicted by coloring a lower part of the display to indicate partial progress toward the goal.

In user interface 1004, it is depicted what might be considered a medium energy expenditure value of 183 to 184 points. This medium value may be presented over a different color background, for example a yellow background, to indicate to the user that progress in energy expenditure points has reached a medium value on the way to a goal or standard. Again, the colored portion of the background may be indicative of the percentage of progress toward a goal or standard.

Referring now to user interface 1006, it is depicted an energy expenditure with a higher point value of 463 to 464 points, which might be considered a high point value. This value may be displayed over a green background, for example, to indicate to the user that they have reached or are close to reaching a goal or standard. The colored background area may fill a larger portion or even all of the background area to indicate the percentage of progress toward a goal or standard.

Figure 11:
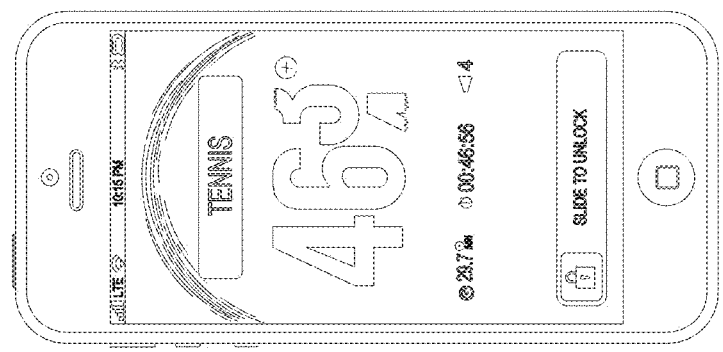
FIG. 11 shows an example view of a UI that may be configured to alter the visual representation or visual indicia based on data collected during one or more sessions.
Figure 11:
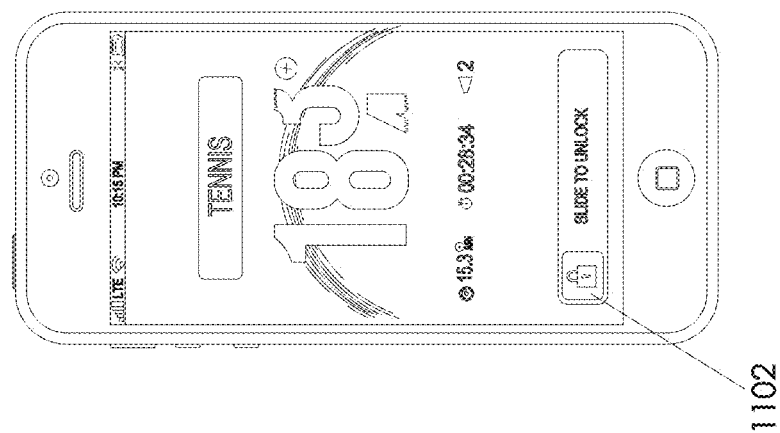
Figure 11:
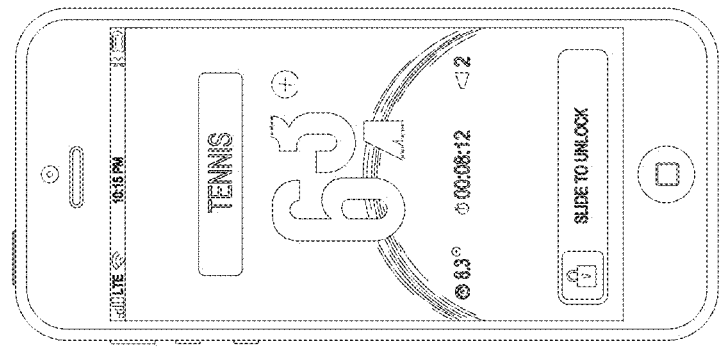

FIG. 11 illustrates the same type of information as in FIG. 10, however, in FIG. 11 it is illustrated how a user interface may display information while also being locked from user input or even as the user is activity using the device associated with the display for another purpose—e.g., another app is active on the display. In some embodiments, the user interface may be locked so that the user is prevented from making inadvertent inputs to the interface. The interface may lock according to various rules. For example, the interface may lock once the session begins or may lock after a delay after the session begins. The user may lock the interface manually, for example, after they have started a session. In some embodiments, the user interface may lock within a certain period of time after a prior user input. As depicted in FIG. 11, one method of unlocking a locked user interface may be to slide the locking icon 1102 to the right, for example, using touch input.

Figure 12:
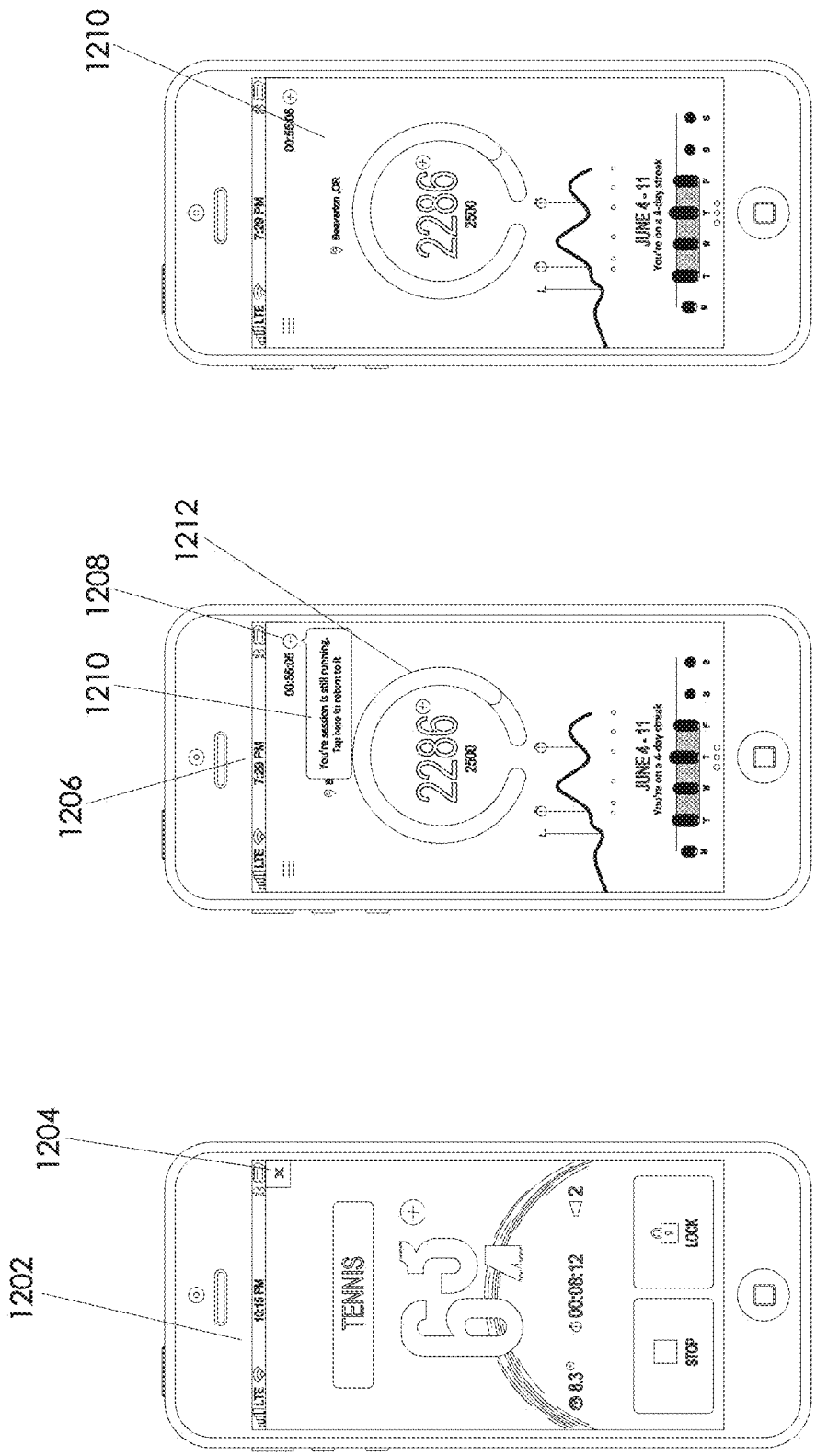
FIG. 12 shows example views of a UI that may be configured to alter the visual representation or visual indicia in view of data collected during one or more sessions and/or permit an interaction by a user in relation to athletic data associated with one or more sessions.

In FIG. 12, user interface 1202 illustrates a session in progress and displayed in the foreground of the user interface. The user interface 1202 provides an exit function by which a user may exit from viewing the session in the foreground. A user may select a user interface item 1204 and cause the display to close the display of the session information and return to another view, such as a home screen or a view of another application on the device. In certain embodiments, the session in this example may still be in progress, however, it may not be displayed in the foreground of the user interface. This may be useful when a user wants to perform some other function on the device, for example. As can be seen in user interface 1206, the session is still running in the background, as indicated by session indicator 1208, but the user can now see a home screen, for example. Note that the home screen view in this example displays the user's cumulative energy expenditure points 1212 for a first time period, e.g., the day. In one embodiment, one or more variables, e.g., an energy expenditure value, heart rate, steps, pace, etc. may be calculated in a period overlapping a session. For example, energy expenditure points may be calculated over a first time period, such as a day or week, and also energy expenditure points may be calculated for a second time period, such as one or more sessions, that overlap with the first time period. In such embodiments, at least a portion of the same athletic data (e.g., energy expenditure) is common to the calculations used in the overlapping time periods. Referring again to FIG. 12, a tool tip 1210 may be displayed to a user to indicate that they may select the session indicator 1208 (an icon or other representation of the background session) in order to bring the display of the session to the foreground.

Referring again to FIG. 12, user interface 1210 depicts what may be referred to as a home screen. As can be seen in 1210, such a home screen may provide information to a user about their total energy expenditure, in addition to the energy expenditure in the session and/or a portion thereof. In the example of 1210, a user has accumulated 2286 energy expenditure points in the day, with a goal to attain 2500 points by the end of the day. A progress bar or other indicator may be used to show the user's progress toward a goal. There may be other indicators to illustrate at what time during the day point were accumulated, as well as how the user is doing, relative to goals, over a previous period, such as a few days or weeks. Progress may be indicated using various methods, including color, progress bars, graphs and numeric representations, among others. Thus, while there may be overlapping calculations for time periods (e.g., a first period being for an entire 24 hour period and second period being for a session within the 24 hour period), they may not be both utilized in the above example, so as to prevent double counting them.

Figure 13:
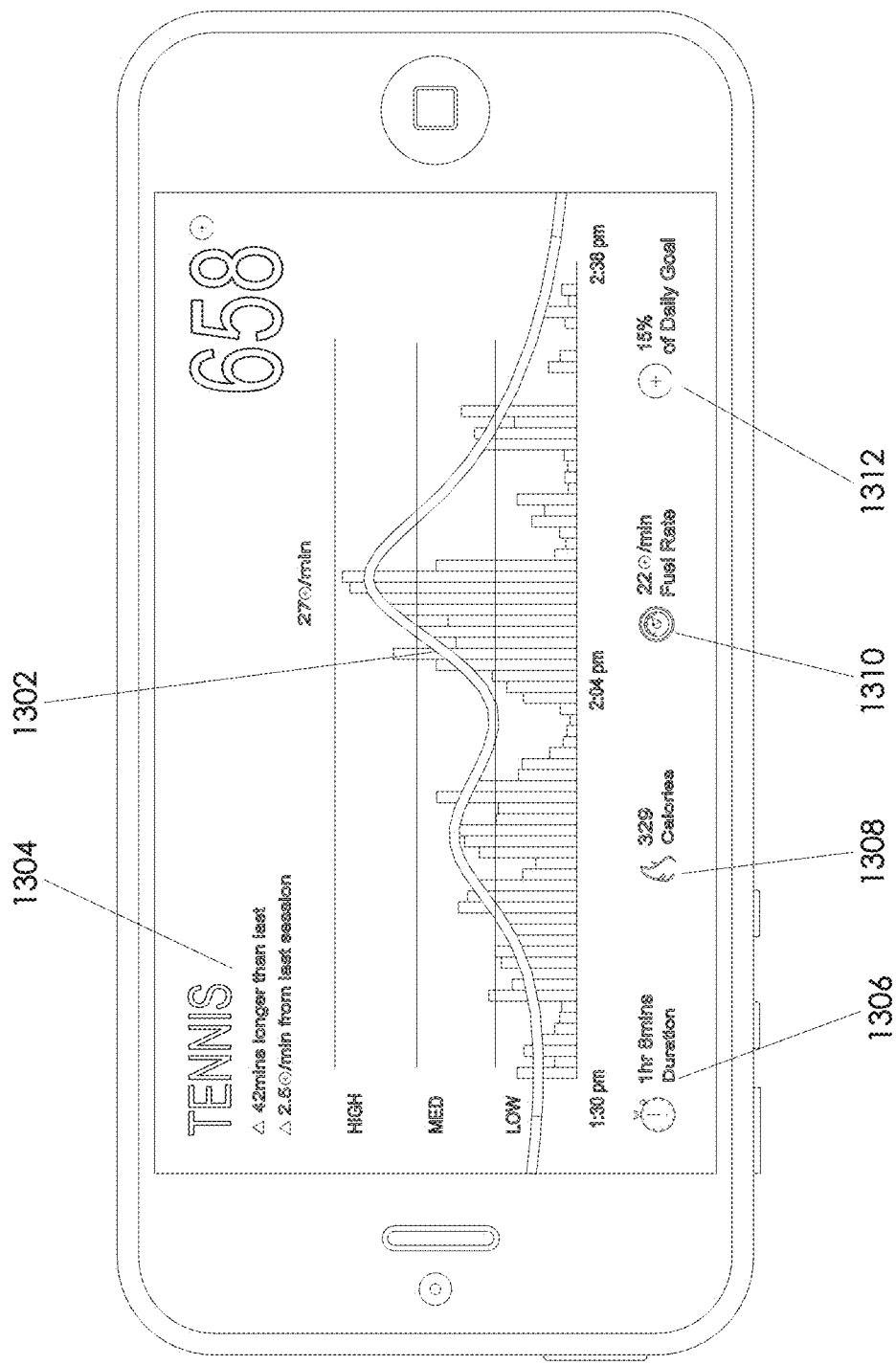
FIG. 13 shows an example view of a UI that may be configured to permit an interaction by a user in relation to athletic data associated with one or more sessions.

FIG. 13 is an example illustration of a session breakdown landscape view. The session breakdown landscape view may provide more detailed information or statistics (and/or different information or statistics) about one or more sessions. For example, graph 1302 may be provided to show a varying level of intensity over time during the session. Milestones or other statistics 1304 may be provided to inform the user how the session compares to other prior sessions. Detailed statistics 1306, 1308, 1310 and 1312 for the session may include items such as the duration, calories burned, percent of a daily energy expenditure point goal.

One or more processes for calculating energy expenditure values, intensity values, and/or other values may be based, at least in part, on the designation of the data. For example, if a session is designated as a yoga session, a first process may be used to calculate energy expenditure, whereas a designation of a soccer game may result in a different process for calculating energy expenditure. Designations may be based upon the user input, sensor data, location, and/or one or more other factors. Further, the designation may result in utilizing (or not utilizing) one or more sensors. One or more collections of data may be re-designated. In certain embodiments, re-designation may result in recalculating at least a portion of the data, such as by using different sensor data, and/or different equations for calculating the values.

Figure 14:
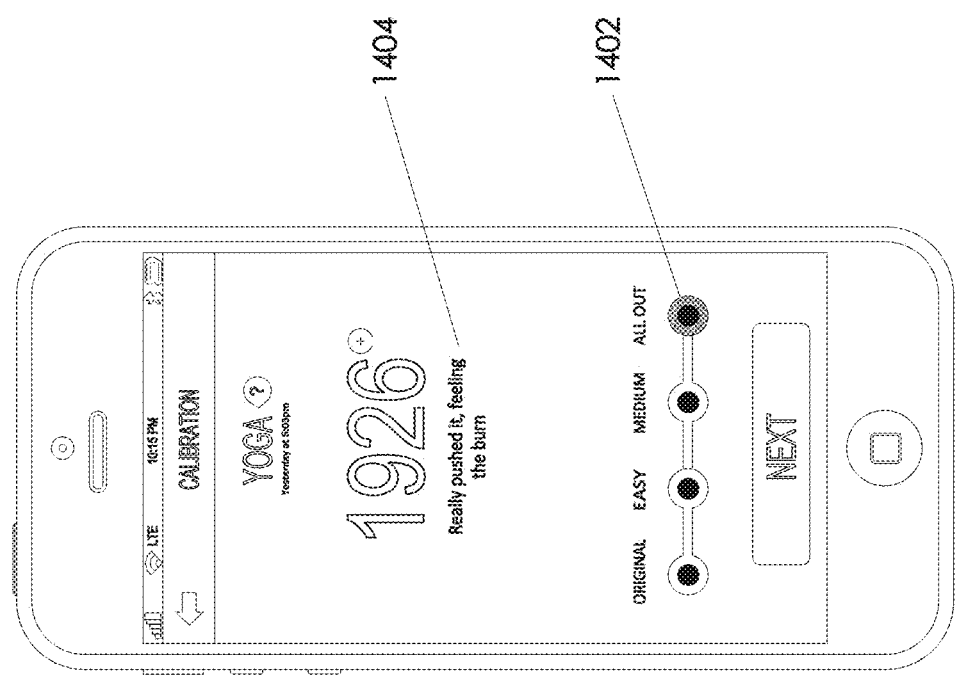
FIG. 14 shows an example view of a UI configured to permit an interaction relating to athletic data associated with one or more sessions.

Certain embodiments may provide for user calibration of sessions. While session may have a default level and/or use a measured intensity level in certain embodiments, calibration may be used to adjust the measured or default intensity level of an activity or session in order to better reflect user's activity. A session may be calibrated immediately upon completion of the session or a session may be selected later and opened for calibration input. FIG. 14 depicts a user interface with a calibration slider 1402 by which a user may adjust the session intensity. In the example given, intensity settings vary from easy to medium to all out. Other intensity settings may be used in various embodiments. In certain embodiments, one or more selections available to the user may be based upon one or more sensor values. Calibration may be particularly useful to a user in activities in which there may be limited or no sensor data, for example, in a swimming session where a sensor might not be used due to the wet environment. Continuing the example, a user after a swimming session may calibrate the session to indicate the level of intensity. In response to changing the intensity setting, a message 1404 may be displayed to the user descriptive of the intensity setting.

Further aspects relate to systems and methods that permit access of a plurality of users to at least a portion of other user's energy expenditure, including for example access to session data of other users. For example, players in a basketball or soccer league may want to compare their energy expenditure levels among teammates and/or one or more opposing players. A collection of motion data (such as session data) may be shared within one more groups. Groups may be implemented such that only a portion of session data (e.g., data collected during a specific time, by a certain sensor, occurring at a certain area, etc.) may be shared with one or more users. Those skilled in the art will appreciate that one or more criteria may dictate sharing properties. Users may create groups, such that an invite from a specific individual or groups of individuals is required for access to certain information. A user may belong to multiple groups and as such, the same or different portions of their activity data (or derivatives thereof) may be shared with different people. A group may provide rankings based upon, for example, total time within sessions, total energy expenditure, energy expenditure meeting specific criterion (e.g., locational criterion), intensity, distance, etc. Further, one or more members of the group may set a group goal, such as earning a specific quantity of energy expenditure during a time period or total time of activity meeting a certain threshold, for example. The goal may permit members to compete against each other to meet a goal, and/or permit at least two members to cooperatively meet one or more goals.

As discussed above, certain embodiments disclosed herein relate to calculating an energy expenditure intensity value. As one example, this value may be determined by quantifying the energy expenditure values for a user for a certain time period. For example, energy expenditure values (or derivatives thereof) a span of time may be used to determine an energy expenditure intensity value for that span of time. Motion data may be obtained from a plurality of different time periods within the time frame. For example, data from a first sensor (which may be an accelerometer, for example) may be obtained every second or multiple times a second and data from a second sensor (such as a force sensor) may be obtained for the same, different or partially overlapping time periods. For example data from the second sensor may be collected at ½ the rate of the first sensor. Data collected at these time points may be used to determine energy expenditure values for specific time periods within the time frame. The time frame is not required to be static. For example, the time period may be rolling consecutive duration of time. Yet, in other embodiments, the time frame may be static.

Certain embodiments may determine whether one or more energy expenditure intensity values meet a threshold during the time frame. Further embodiments may permit one or more users to compete which user or groups of users obtained more energy expenditure during one or more periods. In one embodiment, if a first user meets an intensity threshold level for a duration and a second user does not meet the intensity threshold level for that duration, the first user may be deemed a winner of that duration. If both users met the threshold level, then a tie may be declared. In another embodiment, total energy expenditure over a larger period of time of time that includes the duration(s) in which both users met the threshold level) may be used to determine a winner. In yet other embodiments, whichever user obtained a higher intensity level during the duration or the larger time period of time may be used to determine a winner. Certain embodiments may not utilize data from other actual users. In certain implementations, a virtual AI user may be utilized. Further embodiments may not utilize data from other users, virtual or real, but rather, a user's performance, such as meeting a goal and/or obtaining a virtual reward, may be based solely on whether they achieve a set threshold, regardless of what other user's data indicates and/or if there is not any other user data for comparison. In this regard, the competitions and/or group activities described herein, may be "won" or at least competed in by a single user. For example, a user can "win the day" by obtaining a threshold quantity of hours or time frames in which they met a threshold intensity level. Thus, all disclosure herein relating to comparing a first user's data to a second user's data also is intended to disclose comparing a first user's data to electronically stored data that may not have been collected from actual activity data of another user.

In one embodiment, it may be quantified how many times a user meets a threshold intensity level for a time frame (such as an hour or a day). Systems and methods may be implemented to quantify the number of times a plurality of users each meet a threshold within a set time, such as within with a day. Certain methods may be configured to permit users to compete for instances of meeting a threshold level of intensity in a day or other length of time. As one exemplary embodiment, it may be determined whether any of a plurality of users obtained an intensity threshold level a set amount of time. If a user meets the threshold level for any set duration, which may be measured by ensuring they have a plurality of consecutive expenditure values, then they may get credit for a longer period of time. The quantity of threshold intensity levels meet for the specified durations may be quantified and one or more users may be ranked or otherwise compared. For example, a user may "win the day" if that user met more threshold levels than another user or above a threshold quantity. As discussed above, one or more tie-breakers may be used. Further, as discussed throughout this disclosure, certain criterion may be used to determine whether sensor data is considered and/or how it may be processed. Further, although an exemplary threshold level was discussed, those skilled in the art will appreciate that multiple threshold levels may be used. In one embodiment, a higher threshold intensity level may be weighted in ranking and/or determining a winner.

Further aspects relate to notifying a user when they have or have not met a threshold level or levels. For example, a device may be configured to motivate a user to conduct activity if they have not hit a threshold level for a duration of time. Similarly, a notification may be provided to indicate that they are unlikely to meet a threshold level, such as for a duration of time that includes the current time the user is intended to get the notification. A second reminder, which may be the same or different from the first reminder, could be provided again when less time remains. In one embodiment, the notification may be configured to be generated on a device that comprises at least one sensor that created at least a portion of the user's motion data. In one embodiment, the device may be configured to be worn on an appendage, such as for example, on a user's arm, wrist, or leg. The device may comprise at least one accelerometer for obtaining motion data. In further embodiments, the device may not only generate the notification, but also configured to provide the notification, such as through a display, audio, tactile feedback (e.g., vibrations) and combinations thereof. In other embodiments, the notification may be generated on a first device, such as a computer or portable electronic device and transmitted to a device having at least one of the sensors used to collect the data.

Figure 15C:
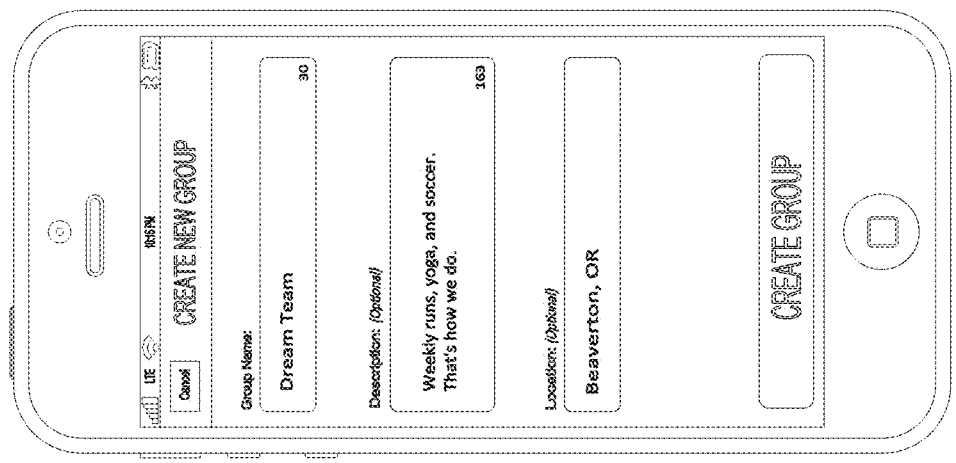
FIGS. 15A-C shows an example view of a UI configured to permit an interaction relating to athletic data associated with one or more sessions, including forming a group.
Figure 15B:
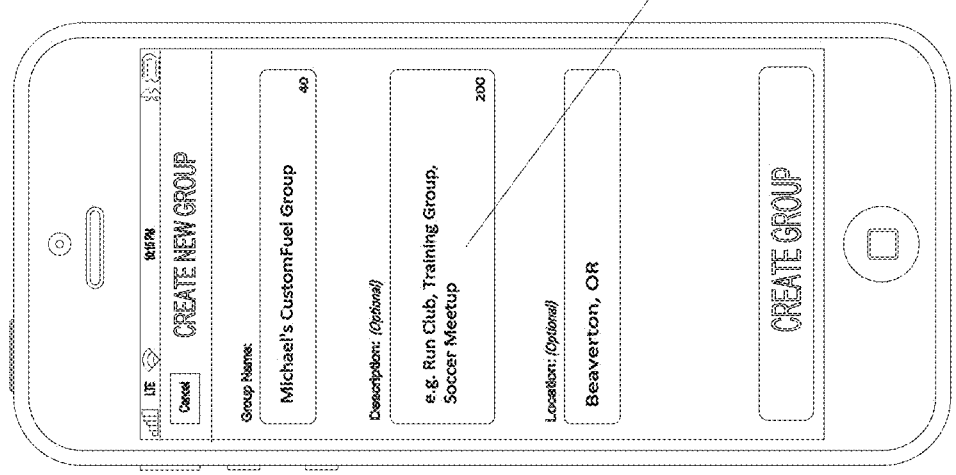
Figure 15A:
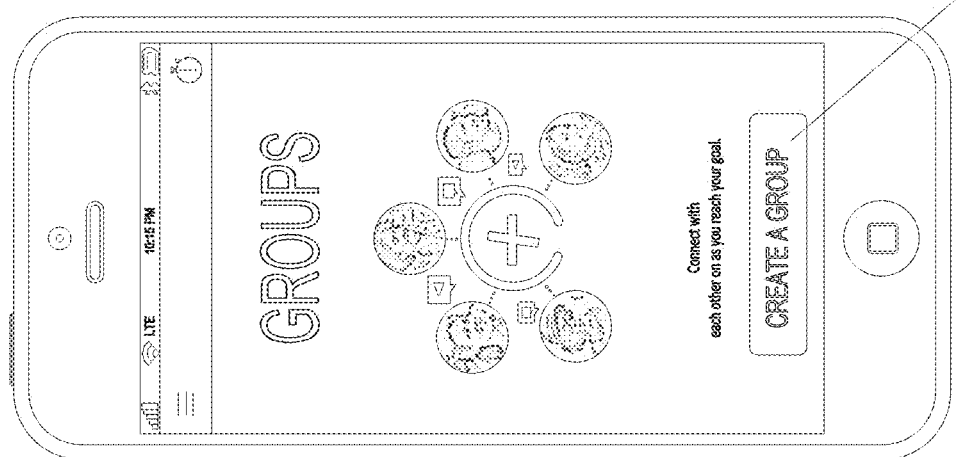

FIGS. 15A-C illustrate an example group creation user interface. User interface select button 1502 may be touched by a user to start the process to create a group. Although a button is shown in FIG. 15A, various other means of accomplishing a selection in a user interface may be used. As can be seen in FIG. 15B, a user may next be presented with input fields 1504 in which a group name, description and location may be entered. Various other information fields may be presented in some embodiments. FIG. 15C illustrates the user interface of FIG. 15B with data populated in the input fields.

Figure 16:
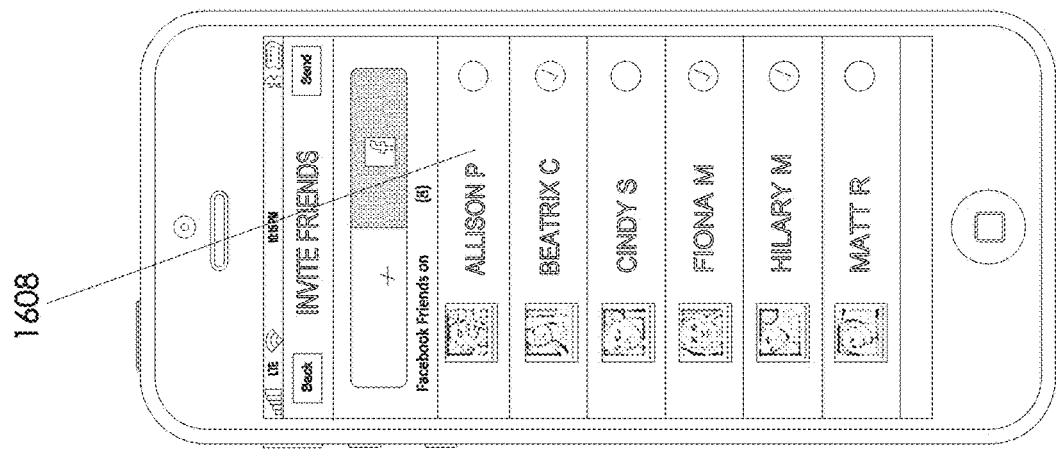
FIG. 16 shows an example view of a UI permit an interaction relating to athletic data associated with one or more sessions, including forming a group.
Figure 16:
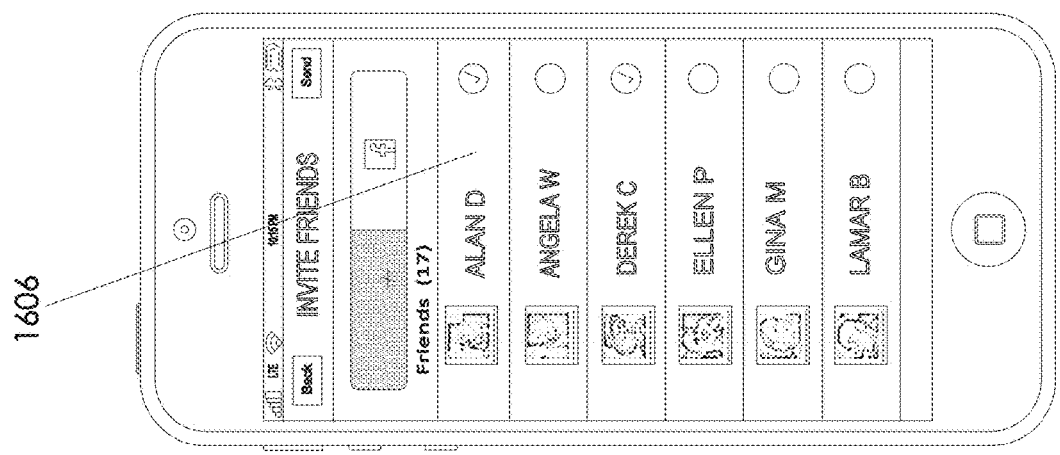
Figure 16:
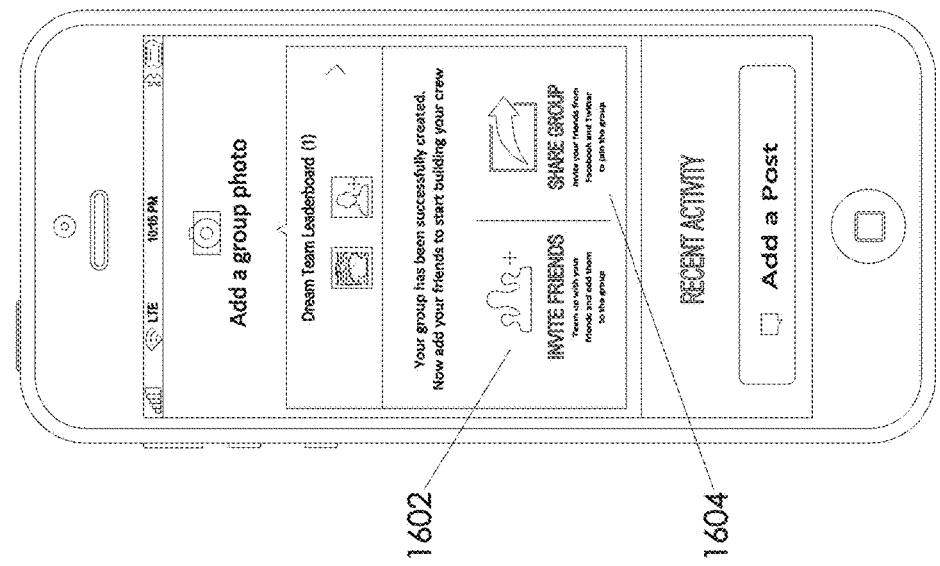

After a user has created a group, friends of the user may be invited to join the group. FIG. 16 illustrates an example where a user's friends may be invited to join the group. After a group has been created, a user may be presented with a user interface 1602 for inviting friends. Upon selecting to invite friends, a listing of friends may next be displayed in the user interface, so that the user may select the friends to add to the group. Friends may be invited from various friend lists, such as a contact list or a social network friend database. Upon selecting the invite option 1602, a user may be presented with a list of friends associated with the selection. As can be seen in FIG. 16, a list of friends from a first listing is presented in 806 and a list of friends from another listing is presented in 1608. Once a user has created a group and invited friends to join the group, the user may share the group with the friends.

Figure 17:
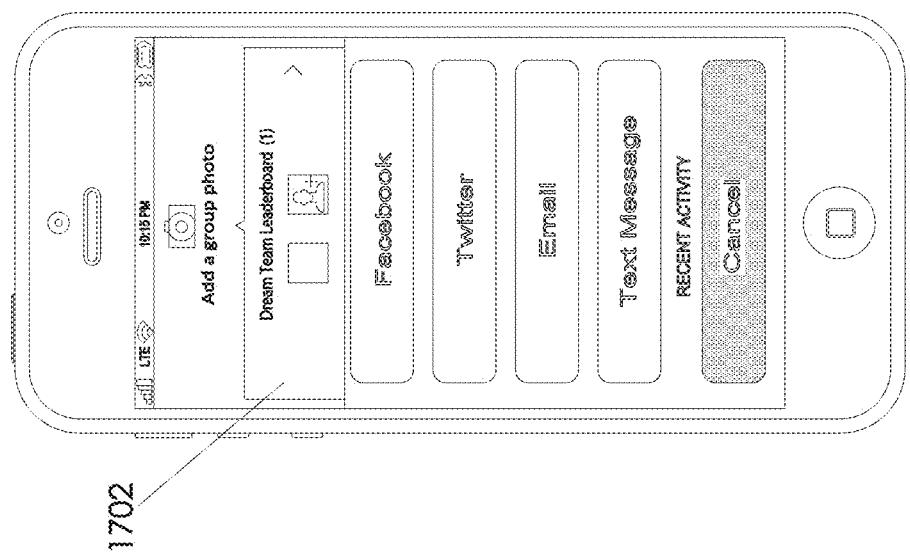
FIG. 17 shows an example view of a UI permit an interaction relating to athletic data associated with one or more sessions, including as part of a group functionality.

Referring again to FIG. 16, a user may also create a web link as another way to share to friends and people to join the group. Continuing the example, a user may tap the "SHARE GROUP" user interface button 1604 to share the group. As illustrated in FIG. 17, showing example UI 1702, the user may next choose to where they would like to share, such as various social networks or communication channels, such as voice, text and/or combination thereof

We claim:

1. A computer-implemented method comprising:
receiving movement data from a sensor of a first device worn by a first user and from a plurality of sensors worn by a plurality of users,
initiating an athletic activity measurement session during a predetermined first time period;
calculating energy expenditure values for the first user and the plurality of users for the predetermined first time period, based on the received movement data;
receiving locational data for the first user from a location-determining sensor of the first device, and for the plurality of users during a second time period within the first time period;
determining an activity type of the first user and an at least one of the plurality of users, based on the received movement data and locational data, wherein the first user and the at least one of the plurality of users are within a predetermined distance of one another;
determining, based on the received locational data that the first user and the at least one of the plurality of users have remained stationary during the second time period and pausing the session; and
transmitting a request to the first user and the at least one of the plurality of users, to form or join a group participating in a common athletic activity.

2. The method of claim 1, further comprising:
for at least the first user and the at least one of the plurality of users, automatically determining a final energy expenditure value for the predetermined first time period; and
displaying the final energy expenditure value for the first predetermined time period on the first device and a device of the at least one of the plurality of users.

3. The method of claim 2, further comprising:
displaying the final energy expenditure value for the predetermined first time period of the first user and the at least one of the plurality of users on the first device and the device of the at least one of the plurality of users.

4. The method of claim 1, further comprising determining that the first user and the at least one of the plurality of users are interested in participating in the common athletic activity, based on the calculated energy expenditure values.

5. The method of claim 1, further comprising:
automatically matching at least a portion of the movement data collected during the predetermined first time period to an activity template; and
automatically classifying the movement data, based on the matching.

6. The method of claim 1, wherein the predetermined first time period is a first time period, and the method further comprising:
after initiation of the calculating the energy expenditure values for the predetermined first time period, initiating a second time clock for measuring athletic activity during the second time period; and
terminating the second time period for both the first user and the at least one of the plurality of users upon determining that an energy expenditure intensity value for one of the first user or the at least one of the plurality of users during the second time period has decreased below a threshold level.

7. The method of claim 1, wherein the predetermined first time period is a first time period, and the method further comprising:
after initiation of the calculating the energy expenditure values for the predetermined first time period, initiating a second time clock for measuring athletic activity during the second time period; and
pausing the second time period for both the first user and the at least one of the plurality of users upon determining that an energy expenditure intensity value for one of the first user or the at least one of the plurality of users during the second time period has decreased below a threshold level.

8. The method of claim 6, further comprising:
categorizing the second time period as a discrete session; and
tagging the session with a date.

9. The method of claim 8, tagging the session with a date comprises:
receiving a user input that provides a tag.

10. The method of claim 8, wherein categorizing the second time period as a discrete session comprises:
receiving a user input configured to add data to the session.

11. The method of claim 6, further comprising:
receiving a user input configured to modify an intensity variable for the movement data collected during the second time period.

12. The method of claim 1, wherein the common athletic activity is part of a league.

13. The method of claim 1, wherein at least a portion of the movement data is received from a sensor embedded in a mobile electronic device.

14. The method of claim 1, further comprising:
classifying a user activity based on a calendar entry.

15. The method of claim 1, further comprising:
suggesting a set of classifications for a user activity.

16. The method of claim 15, wherein the suggesting is based on at least one of an environmental attribute or a user attribute.

17. An apparatus comprising:
a processor; and
a non-transitory computer-readable medium comprising computer-executable instructions that when executed by the processor cause the apparatus to:
receive movement data from a sensor of a first device worn by a first user and from a plurality of sensors worn by a plurality of users,
initiate an athletic activity measurement session during a predetermined first time period;
calculate energy expenditure values for the first user and the plurality of users for the predetermined first time period, based on the received movement data;
receive locational data for the first user from a location-determining sensor of the first device, and for the plurality of users during a second time period within the first time period;
determine an activity type of the first user and an at least one of the plurality of users, based on the received movement data and locational data, wherein the first user and the at least one of the plurality of users are within a predetermined distance of one another;
determine, based on the received locational data that the first user and the at least one of the plurality of users have remained stationary during the second time period and pausing the session; and
transmit a request to the first user and the at least one of the plurality of users, to form or join a group participating in a common athletic activity.

18. The apparatus of claim 17, the non-transitory computer-readable medium comprising computer-executable instructions that when executed by the processor cause the apparatus to:
- for at least the first user and the at least one of the plurality of users, automatically determine a final energy expenditure value for the predetermined first time period; and
- display the final energy expenditure value for the first predetermined time period on the first device and a device of the at least one of the plurality of users.

19. The apparatus of claim 18, the non-transitory computer-readable medium comprising computer-executable instructions that when executed by the processor cause the apparatus to:
- displaying the final energy expenditure value for the predetermined first time period of the first user and the at least one of the plurality of users on the first device and the device of the at least one of the plurality of users.

20. The apparatus of claim 17, the non-transitory computer-readable medium comprising computer-executable instructions that when executed by the processor cause the apparatus to:
- determine that the first user and the at least one of the plurality of users are interested in participating in the common athletic activity, based on the calculated energy expenditure values.

* * * * *